(12) United States Patent
Dayton et al.

(10) Patent No.: US 10,973,499 B2
(45) Date of Patent: Apr. 13, 2021

(54) ARTICULATING NEEDLES AND RELATED METHODS OF USE

(71) Applicant: Boston Scientific Scimed, Inc., Maple Grove, MN (US)

(72) Inventors: Peter L. Dayton, Brookline, MA (US); Ryan V. Wales, Northborough, MA (US); Sean P. Fleury, Minneapolis, MN (US); Paul Smith, Smithfield, RI (US); Scott E. Brechbiel, Acton, MA (US); Kevin Mcelwee, Franklin, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 355 days.

(21) Appl. No.: 15/901,019

(22) Filed: Feb. 21, 2018

(65) Prior Publication Data
US 2018/0242958 A1 Aug. 30, 2018

Related U.S. Application Data

(60) Provisional application No. 62/464,785, filed on Feb. 28, 2017.

(51) Int. Cl.
A61B 10/02 (2006.01)
A61B 10/04 (2006.01)
(Continued)

(52) U.S. Cl.
CPC ...... *A61B 10/0233* (2013.01); *A61B 10/0283* (2013.01); *A61B 10/04* (2013.01); *A61B 17/3478* (2013.01); *A61B 1/008* (2013.01); *A61B 1/0055* (2013.01); *A61B 1/00078* (2013.01); *A61B 2010/045* (2013.01); *A61B 2017/00314* (2013.01); *A61B 2017/3443* (2013.01); *A61B 2090/508* (2016.02); *A61M 5/329* (2013.01)

(58) Field of Classification Search
CPC ............... A61B 10/0233; A61B 10/04; A61B 2017/00315; A61B 2017/2332; A61B 2010/045; A61B 1/008; A61B 1/00078; A61B 1/0055; A61B 2017/00314; A61B 2017/3443; A61M 5/329
See application file for complete search history.

(56) References Cited

U.S. PATENT DOCUMENTS 4,187,861 A * 2/1980 Heffernan ............. B01L 3/5082
422/913
4,353,358 A * 10/1982 Emerson ............... A61B 1/0056
600/139
(Continued)

FOREIGN PATENT DOCUMENTS

WO 2012151398 A2 11/2012

*Primary Examiner* — Sean P Dougherty
(74) *Attorney, Agent, or Firm* — Bookoff McAndrews, PLLC

(57) ABSTRACT

A medical device may include a needle, including a plurality of links and a distal tip, reciprocally movable between a first configuration and a second configuration, and a conduit including a lumen extending through the needle, the conduit being coupled to the distal tip, wherein longitudinal movement of the conduit is configured to transition the needle between the first configuration and the second configuration.

16 Claims, 11 Drawing Sheets

(51) Int. Cl.
*A61B 17/34* (2006.01)
*A61M 5/32* (2006.01)
*A61B 90/50* (2016.01)
*A61B 17/00* (2006.01)
*A61B 1/005* (2006.01)
*A61B 1/008* (2006.01)
*A61B 1/00* (2006.01)

(56) References Cited

U.S. PATENT DOCUMENTS

| | | | | |
|---|---|---|---|---|
| 4,708,134 A * | 11/1987 | Wildemeersch | A61F 6/142 | 128/840 |
| 4,796,607 A * | 1/1989 | Allred, III | A61B 1/0055 | 138/120 |
| 4,911,148 A * | 3/1990 | Sosnowski | A61B 1/0051 | 600/136 |
| 5,219,338 A * | 6/1993 | Haworth | A61M 5/326 | 604/198 |
| 5,228,441 A * | 7/1993 | Lundquist | A61B 18/1492 | 600/380 |
| 5,549,571 A * | 8/1996 | Sak | A61M 25/0637 | 604/198 |
| 5,658,256 A * | 8/1997 | Shields | A61M 5/3202 | 604/192 |
| 5,766,196 A * | 6/1998 | Griffiths | A61B 17/29 | 600/564 |
| 5,807,241 A * | 9/1998 | Heimberger | A61B 1/0055 | 600/139 |
| 5,873,817 A * | 2/1999 | Kokish | A61B 1/0058 | 600/143 |
| 5,916,147 A * | 6/1999 | Boury | A61M 25/0147 | 600/139 |
| 6,270,453 B1 * | 8/2001 | Sakai | A61B 1/0055 | 600/141 |
| 6,375,640 B1 * | 4/2002 | Teraoka | A61M 25/0625 | 604/162 |
| 6,717,092 B2 * | 4/2004 | Obata | A61B 1/0011 | 219/127 |
| 6,743,239 B1 * | 6/2004 | Kuehn | A61B 17/0643 | 464/149 |
| 6,969,392 B2 * | 11/2005 | Gitis | A61B 17/3403 | 606/87 |
| 6,974,411 B2 * | 12/2005 | Belson | A61B 1/00078 | 600/114 |
| 7,004,213 B2 * | 2/2006 | Hansen | A61J 1/2089 | 141/329 |
| 7,137,949 B2 * | 11/2006 | Scirica | A61B 17/0293 | 600/229 |
| 7,785,252 B2 * | 8/2010 | Danitz | A61B 1/0055 | 600/142 |
| 7,862,554 B2 * | 1/2011 | Hegeman | A61B 1/0055 | 606/1 |
| 8,105,350 B2 * | 1/2012 | Lee | A61B 1/00071 | 606/205 |
| 8,114,097 B2 * | 2/2012 | Brock | A61B 34/35 | 606/130 |
| 8,298,161 B2 * | 10/2012 | Vargas | A61M 25/00 | 600/587 |
| 8,323,241 B2 * | 12/2012 | Salahieh | A61M 25/0136 | 604/95.04 |
| 8,403,832 B2 * | 3/2013 | Cunningham | A61B 18/1445 | 600/141 |
| 8,968,312 B2 * | 3/2015 | Marczyk | A61B 17/29 | 606/51 |
| 9,011,318 B2 * | 4/2015 | Choset | A61B 17/00234 | 600/114 |
| 9,144,370 B2 * | 9/2015 | Kato | A61B 1/008 | |
| 9,233,225 B2 * | 1/2016 | Hebert | A61M 25/0138 | |
| 9,282,993 B1 * | 3/2016 | Cohen | A61B 17/3421 | |
| 9,408,529 B2 * | 8/2016 | Smith | A61B 1/00098 | |
| 9,820,634 B2 * | 11/2017 | Simchony | A61B 10/04 | |
| 9,839,443 B2 * | 12/2017 | Brockman | A61B 17/3478 | |
| 9,993,266 B2 * | 6/2018 | Lenker | A61B 17/3478 | |
| 10,022,877 B2 * | 7/2018 | Wang | B25J 18/06 | |
| 10,034,683 B2 * | 7/2018 | Monroe | A61B 17/295 | |
| 10,258,363 B2 * | 4/2019 | Worrell | A61B 17/320068 | |
| 10,350,372 B2 * | 7/2019 | Centeno | A61B 17/3478 | |
| 10,420,537 B2 * | 9/2019 | Salahieh | A61B 17/00234 | |
| 10,513,240 B2 * | 12/2019 | Stegerer | F16G 13/20 | |
| 10,548,628 B2 * | 2/2020 | Swaney | A61B 17/3403 | |
| 10,610,345 B2 * | 4/2020 | Cardinale | A61B 17/0682 | |
| 2003/0114797 A1 * | 6/2003 | Vaillancourt | B29C 48/16 | 604/171 |
| 2003/0160712 A1 * | 8/2003 | Levy | H01H 13/702 | 341/22 |
| 2003/0233057 A1 * | 12/2003 | Saadat | A61B 1/00135 | 600/585 |
| 2004/0044270 A1 * | 3/2004 | Barry | A61B 1/0056 | 600/142 |
| 2004/0249367 A1 * | 12/2004 | Saadat | A61B 1/018 | 606/1 |
| 2005/0067459 A1 * | 3/2005 | Swayze | A61B 17/07207 | 227/176.1 |
| 2005/0131279 A1 | 6/2005 | Boulais et al. | | |
| 2005/0137455 A1 * | 6/2005 | Ewers | A61B 1/0055 | 600/114 |
| 2005/0137456 A1 * | 6/2005 | Saadat | A61B 1/31 | 600/114 |
| 2006/0058582 A1 * | 3/2006 | Maahs | A61B 1/00154 | 600/144 |
| 2006/0064101 A1 * | 3/2006 | Arramon | A61B 17/8811 | 606/82 |
| 2006/0074407 A1 * | 4/2006 | Padget | A61B 17/3201 | 606/1 |
| 2006/0293612 A1 * | 12/2006 | Jenson | A61B 17/3207 | 600/585 |
| 2007/0015965 A1 * | 1/2007 | Cox | A61B 1/0052 | 600/114 |
| 2007/0088340 A1 * | 4/2007 | Brock | A61B 34/70 | 606/1 |
| 2007/0093840 A1 * | 4/2007 | Pacelli | A61B 17/1631 | 606/80 |
| 2007/0135803 A1 * | 6/2007 | Belson | A61B 5/064 | 606/1 |
| 2008/0064921 A1 * | 3/2008 | Larkin | A61B 1/00154 | 600/104 |
| 2008/0091170 A1 * | 4/2008 | Vargas | A61M 25/0105 | 604/528 |
| 2008/0208255 A1 * | 8/2008 | Siegal | A61B 17/1757 | 606/246 |
| 2009/0131886 A1 | 5/2009 | Liu et al. | | |
| 2009/0299302 A1 * | 12/2009 | Lambert | A61M 5/158 | 604/263 |
| 2010/0082033 A1 | 4/2010 | Germain | | |
| 2010/0249759 A1 * | 9/2010 | Hinman | A61B 17/00 | 606/1 |
| 2011/0028991 A1 * | 2/2011 | Ikeda | A61B 1/008 | 606/130 |
| 2011/0071508 A1 * | 3/2011 | Duval | A61B 1/00183 | 606/1 |
| 2011/0184241 A1 * | 7/2011 | Zubiate | A61B 34/30 | 600/141 |
| 2011/0282149 A1 * | 11/2011 | Vargas | A61M 25/0105 | 600/114 |
| 2011/0313243 A1 * | 12/2011 | Zubiate | A61B 1/04 | 600/104 |
| 2011/0313357 A1 * | 12/2011 | Skutnik | A61M 5/46 | 604/151 |
| 2012/0016367 A1 * | 1/2012 | Chabansky | A61B 17/1642 | 606/79 |
| 2012/0071720 A1 * | 3/2012 | Banik | A61B 1/00045 | 600/118 |
| 2012/0191090 A1 | 7/2012 | Sugahara et al. | | |
| 2012/0197239 A1 * | 8/2012 | Smith | A61B 1/0055 | 606/1 |
| 2012/0232567 A1 * | 9/2012 | Fairneny | A61B 17/0482 | 606/147 |

(56) References Cited

U.S. PATENT DOCUMENTS

| | | | | |
|---|---|---|---|---|
| 2012/0277730 A1* | 11/2012 | Salahieh | ............ | A61B 1/00135 |
| | | | | 604/527 |
| 2013/0023915 A1* | 1/2013 | Mueller | ................. | A61B 17/29 |
| | | | | 606/170 |
| 2013/0267936 A1* | 10/2013 | Stroup | ............. | A61B 17/00234 |
| | | | | 606/1 |
| 2013/0296885 A1* | 11/2013 | Desai | .................. | A61B 17/3421 |
| | | | | 606/130 |
| 2014/0012287 A1* | 1/2014 | Oyola | ..................... | A61B 34/76 |
| | | | | 606/130 |
| 2014/0107420 A1* | 4/2014 | Konno | ..................... | A61B 1/31 |
| | | | | 600/114 |
| 2014/0166718 A1* | 6/2014 | Swayze | .............. | A61B 17/1155 |
| | | | | 227/175.1 |
| 2014/0243592 A1* | 8/2014 | Kato | ................. | A61M 25/0147 |
| | | | | 600/104 |
| 2015/0094612 A1* | 4/2015 | Miyazaki | ............... | A61B 10/06 |
| | | | | 600/564 |
| 2015/0150633 A1* | 6/2015 | Castro | .................... | A61B 17/29 |
| | | | | 606/130 |
| 2015/0238733 A1* | 8/2015 | bin Abdulla | ...... | A61M 25/0637 |
| | | | | 604/263 |
| 2015/0320437 A1* | 11/2015 | Worrell | .................... | A61N 7/00 |
| | | | | 606/169 |
| 2015/0328435 A1 | 11/2015 | Mathis et al. | | |
| 2015/0374211 A1* | 12/2015 | Smith | ...................... | A61B 1/01 |
| | | | | 600/114 |
| 2016/0022313 A1* | 1/2016 | Yoshida | ............. | A61B 17/3478 |
| | | | | 606/185 |
| 2016/0100860 A1* | 4/2016 | Lenker | ............... | A61B 17/3478 |
| | | | | 604/95.01 |
| 2016/0151608 A1* | 6/2016 | Aklog | ............... | A61M 25/0009 |
| | | | | 604/506 |
| 2016/0310702 A1 | 10/2016 | Cabiri | | |
| 2017/0095922 A1* | 4/2017 | Licht | ...................... | A61B 34/30 |
| 2017/0157361 A1* | 6/2017 | Barrish | ................. | A61B 34/20 |
| 2018/0078354 A1* | 3/2018 | Cardinale | .......... | A61B 17/0682 |
| 2018/0250053 A1* | 9/2018 | Schultz | .............. | A61B 17/8861 |

* cited by examiner

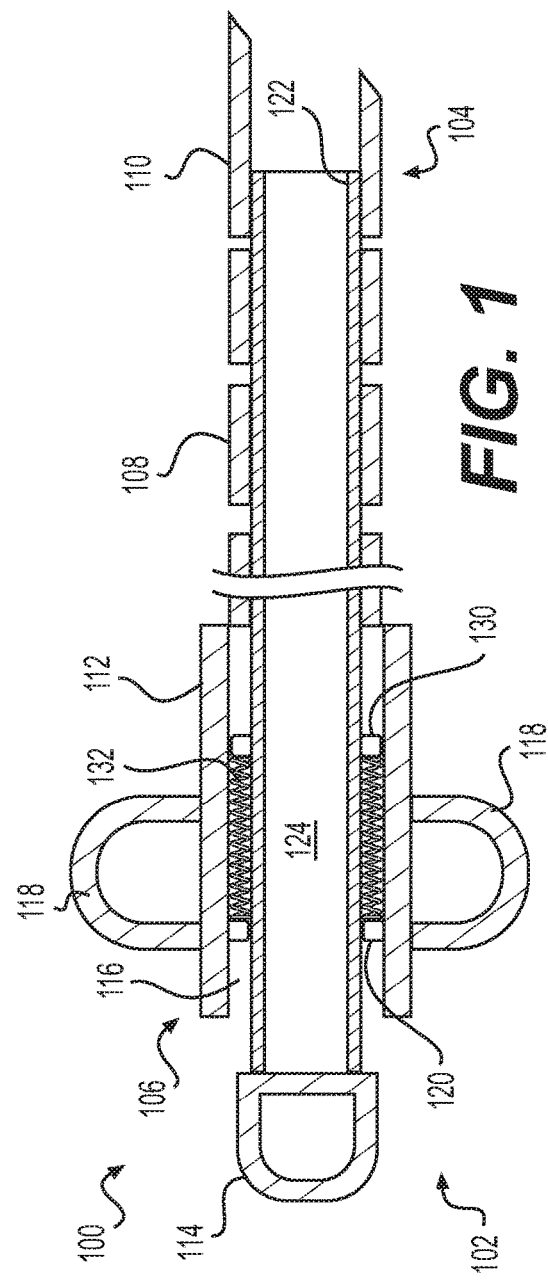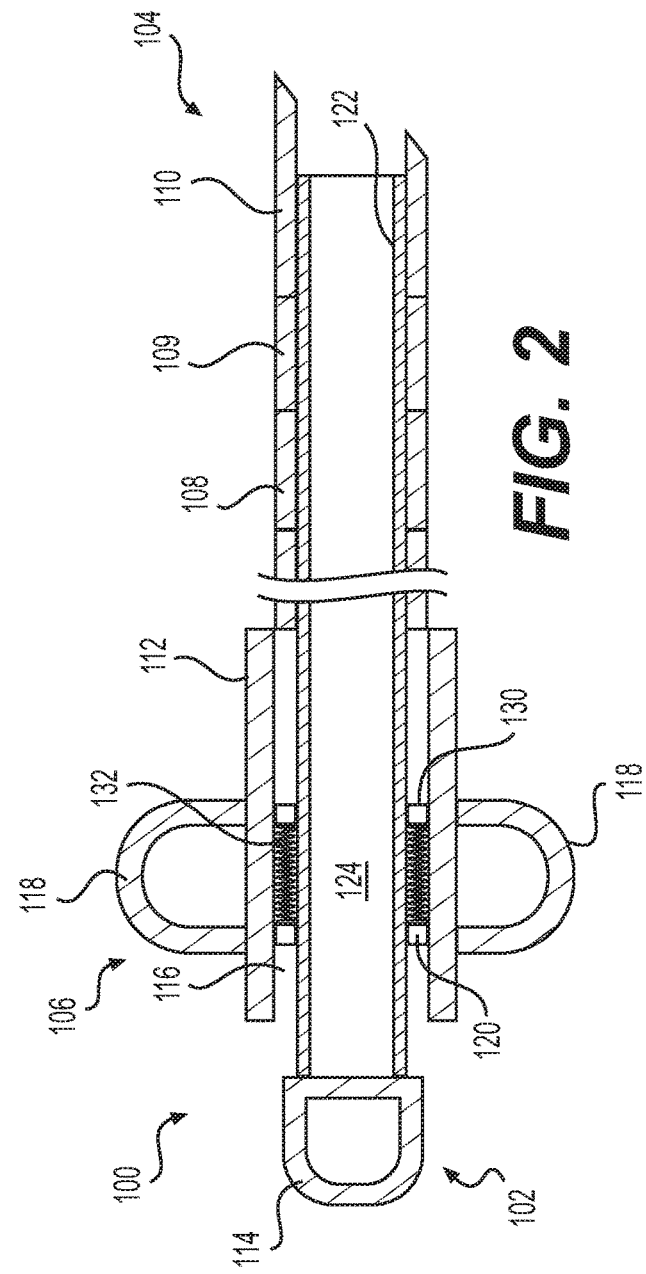

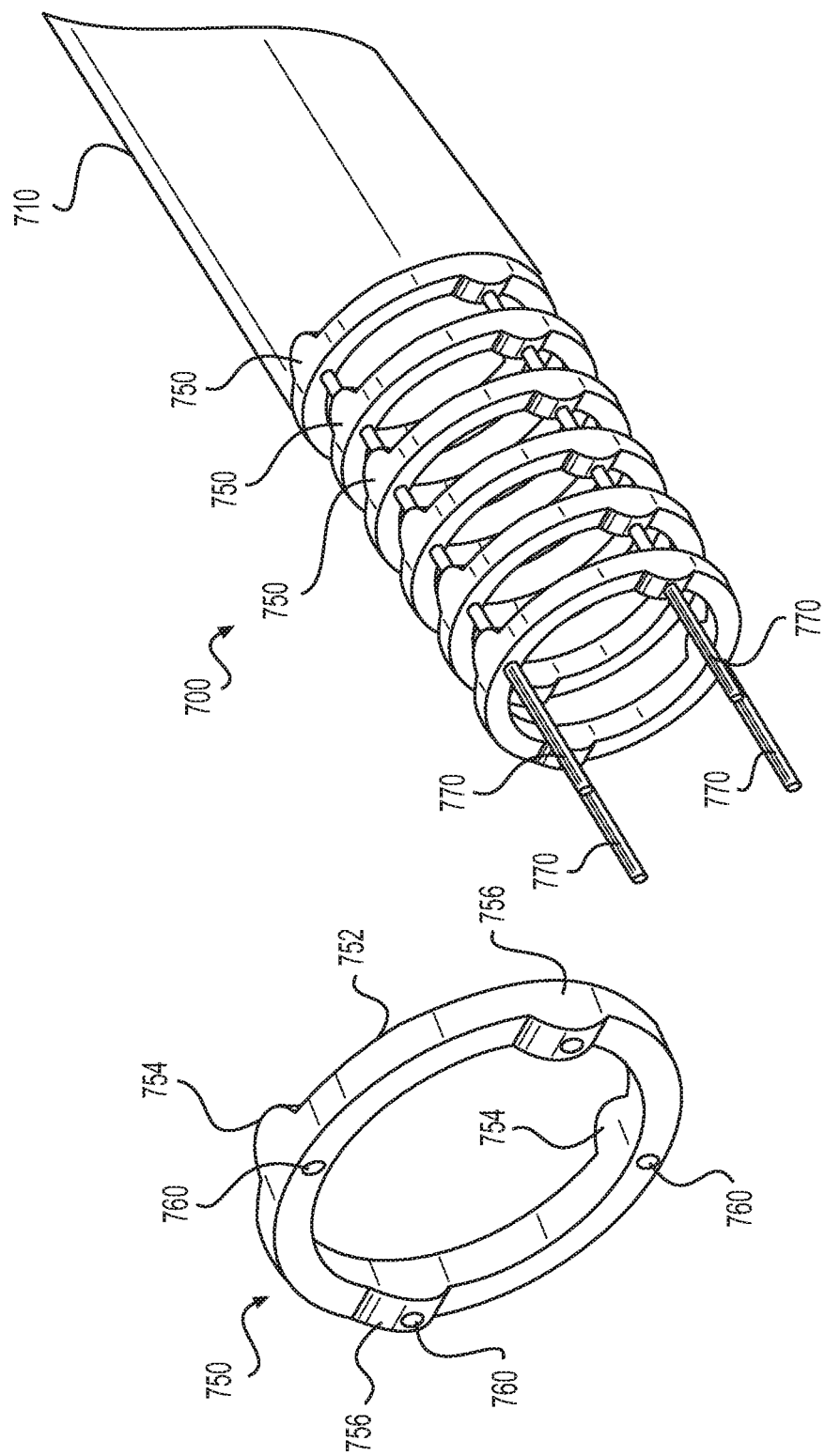

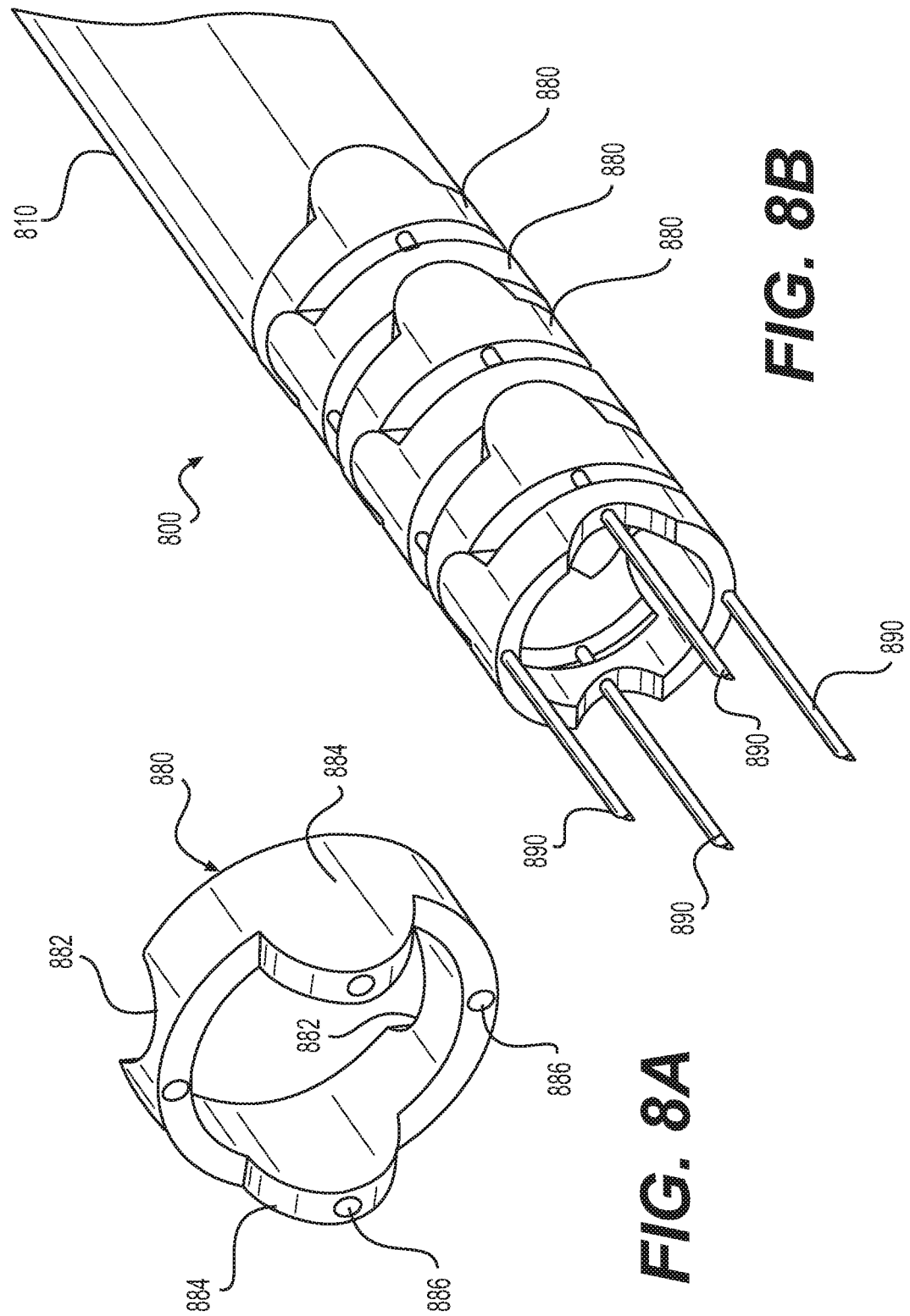

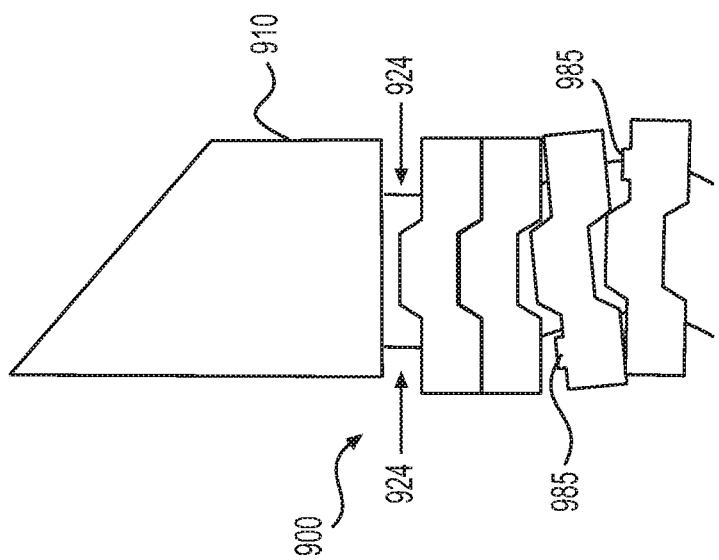
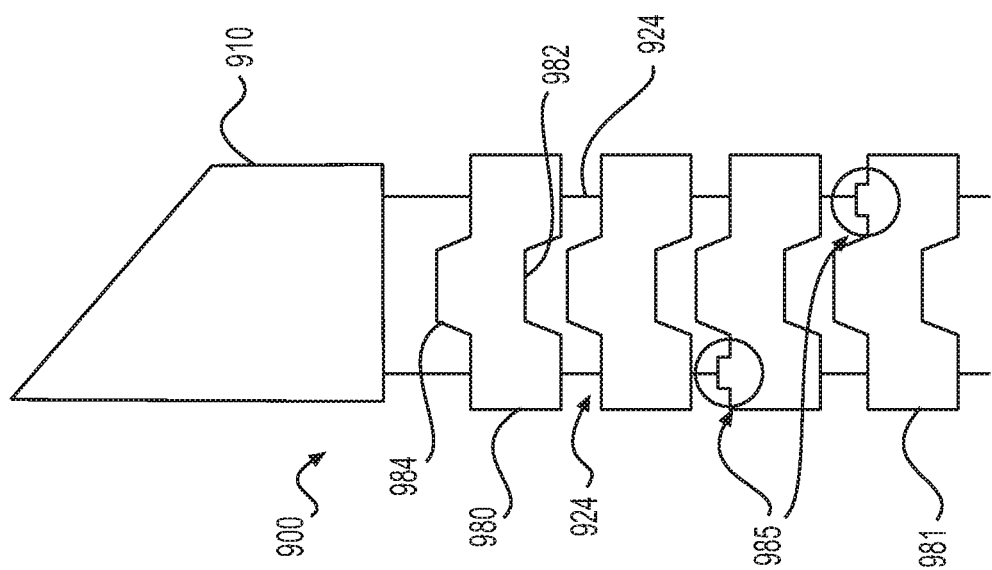

ARTICULATING NEEDLES AND RELATED METHODS OF USE

CROSS-REFERENCE TO RELATED APPLICATION(S)

This patent application claims the benefit under 35 U.S.C. § 119 to U.S. Provisional Patent Application No. 62/464,785, filed on Feb. 28, 2017, the entirety of which is incorporated herein by reference.

TECHNICAL FIELD

Aspects of the present disclosure relate to articulating needles, and related methods of use.

INTRODUCTION

A biopsy entails the surgical removal of tissue or cells from the body of a patient for pathological examination of the collected sample. A purpose of taking a biopsy sample is often to look for cellular shape changes represented in the collected sample. The identification of particular cellular shape changes in a collected specimen can be instrumental in the identification of cancer in a patient.

Endoscopes are often used to access and visualize a patient's anatomical lumen during a medical procedure. Once the endoscope is positioned in the desired body portion, a biopsy instrument can be advanced through the working channel of the endoscope to the desired body portion. The endoscopic and biopsy instruments then may be manipulated as desired for visualization and specimen sampling, respectively.

Smaller diameter endoscopes help reduce unnecessary trauma to the tissues of a patient, and provide access to more diverse categories of patient body lumens. These endoscopes often have smaller working channels, which limit the size of auxiliary instruments that can be used with the endoscope. This, in turn, limits the size, and often the quality of, any biopsy specimen collected.

A needle biopsy can be performed with a stylet-needle shaft having a tissue retaining recess formed in a lateral side of the area close to the needle tip. When the needle is inserted into tissue from which a sample is desired, a portion of tissue extends into the recess. Such needle biopsy devices often cannot be positioned in flexible small diameter positioning devices because the puncturing stylet-needle is rigid.

SUMMARY

In one aspect, the present disclosure is directed to a medical device. The medical device may include a needle, including a plurality of links and a distal tip, reciprocally movable between a first configuration and a second configuration, and a conduit including a lumen extending through the needle, the conduit being coupled to the distal tip, wherein longitudinal movement of the conduit is configured to transition the needle between the first configuration and the second configuration.

The needle may have a first rigidity in the first configuration, and a second rigidity greater than the first rigidity in the second configuration. Application of a force to the distal tip in the first configuration may cause the plurality of links and the distal tip to change orientation relative to one another, and application of the force to the distal tip in the second configuration may not cause the plurality of links and the distal tip to change orientation relative to one another. Fluid flow through the needle may pass through the lumen of the conduit, and may exit the needle only at the distal tip. The plurality of links may ride loosely along an outer surface of the conduit in the first configuration. The medical device may include a spring configured to bias the needle into the first configuration. A proximal force applied to the conduit while the needle is in the first configuration may compress the spring and transition the needle into the second configuration. Release of the proximal force while the needle is in the second configuration may allow the needle to transition back to the first configuration. The medical device may include a handle having a body, an actuator movable relative to the body, a first stop on an outer surface of the conduit, a second stop extending radially inward from an inner surface of the body, wherein the spring may be between the first stop and the second stop. The conduit may be coupled to a distal end of the actuator. The longitudinal movement of the conduit may be relative to the plurality of links. The conduit may be fixed to the distal tip. At least one of the plurality of links may have a protrusion that engages a surface of an adjacent link. The needle may include a radius of curvature in the second configuration. The needle may have a greater length in the first configuration than in the second configuration. The needle tip may include a distalmost point splayed radially outward from a remainder of the distal tip, wherein the distalmost point may be located at an end of a path that travels along an entirety of the needle.

In another aspect, the present disclosure is directed to a medical device. The medical device may include a needle, including a plurality of links and a distal tip, reciprocally movable between a first configuration and a second configuration, wherein second configuration may be more rigid than the first configuration, a conduit including a lumen extending through the needle, the conduit being fixed to the distal tip, wherein application of a proximal pulling force on the conduit may be configured to transition the needle from the first configuration and the second configuration, and release of the proximal pulling force may be configured to transition the needle from the second configuration to the first configuration.

Application of a force to the distal tip in the first configuration may cause the plurality of links and the distal tip to change orientation relative to one another, and application of the force to the distal tip in the second configuration may not cause the plurality of links and the distal tip to change orientation relative to one another. Fluid flow through the needle may pass through the lumen of the conduit, and may exit the needle only at the distal tip.

In yet another aspect, the present disclosure is directed to a medical device. The medical device may include a needle, including a plurality of links and a distal tip, reciprocally movable between a first configuration and a second configuration, wherein the needle may have a radius of curvature in the second configuration and may include a distalmost point splayed radially outward from a remainder of the distal tip, the distalmost point being located at an end of a path that travels along an entirety of the needle, and a conduit including a lumen extending through the needle, the conduit being fixed to the distal tip, wherein application of a proximal pulling force on the conduit may be configured to transition the needle from the first configuration and the second configuration, and release of the proximal pulling force may be configured to transition the needle from the second configuration to the first configuration.

Fluid flow through the needle may pass through the lumen of the conduit, and may exit the needle only at the distal tip.

BRIEF DESCRIPTION OF THE DRAWINGS

The accompanying drawings, which are incorporated in and constitute a part of this specification, illustrate various aspects and together with the description, serve to explain the principles of the disclosed aspects.

FIG. 1 is a side cross-sectional view of a medical device in a first configuration, according to an aspect of the present disclosure.

FIG. 2 is a side cross-sectional view of the medical device of FIG. 1 in a second configuration.

FIG. 7A is a perspective view of a link according to an aspect of the present disclosure.

FIG. 7B is a perspective view of a needle according to an aspect of the present disclosure.

FIG. 8A is a perspective view of a link according to an aspect of the present disclosure.

FIG. 8B is a perspective view of a needle according to an aspect of the present disclosure.

FIG. 9A is a side view of a needle in a first configuration, according to an aspect of the present disclosure.

FIG. 9B is a side view of the needle of FIG. 9A in a second configuration.

DETAILED DESCRIPTION

Figure 3:
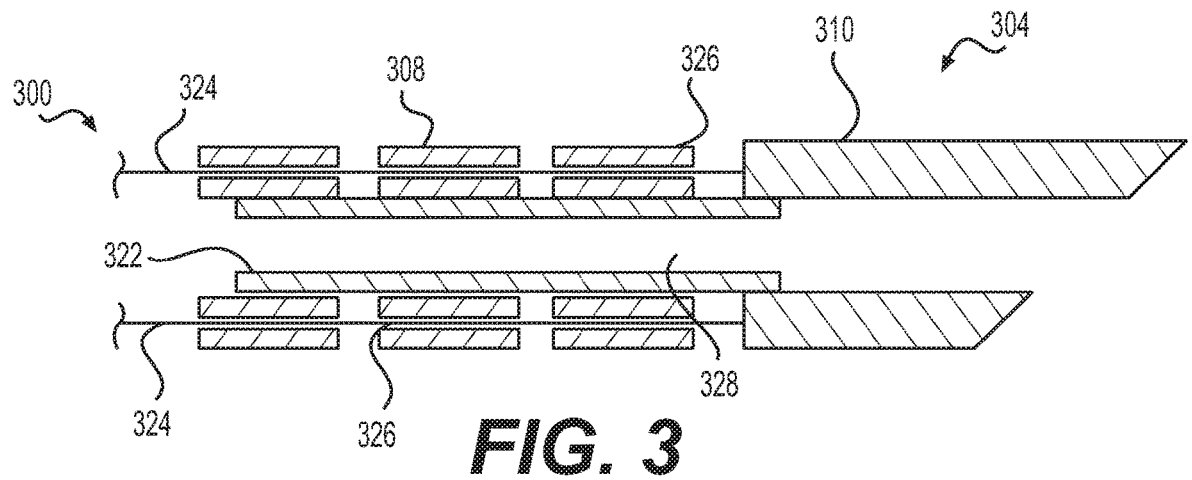
FIG. 3 is a side cross-sectional view of a medical device in a first configuration, according to another aspect of the present disclosure.

Reference will now be made in detail to aspects of the present disclosure, which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body.

Aspects of the present disclosure are directed to medical devices configured to pass through a scope in a loose, flexible state, and extend beyond the distal end of the scope in a rigid state to perform various medical procedures, such as, e.g., collecting tissue in a biopsy procedure or deflecting tissue from one location to another. The ability for a device to hold multiple configurations with different sizes and stiffnesses can enable the devices to be optimized for travel through tortuous anatomy in the flexible state, and optimized for performing a clinical task when positioned distal to the distal end of the scope in the rigid state.

A medical device 100 is shown in a first, loose configuration in FIG. 1, and in a second, rigid configuration in FIG. 2. Medical device 100 may be reciprocally movable between the first and second configurations, and also may be configured to extend through an endoscopic device. Medical device 100 may extend from a proximal end 102 toward a distal end 104. Medical device 100 may include a handle 106 at proximal end 102, a plurality of links 108, and a distal tip 110. The plurality of links 108 and the distal tip 110 may form a needle 109 when medical device 100 is in the second configuration of FIG. 2.

Handle 106 may include a body 112, and an actuator 114 that is slidable or otherwise movable relative to body 112. Body 112 may include a lumen 116, and two diametrically opposed grips 118. Grips 118, in some aspects, may be held by a physician or other suitable operators using the index and middle fingers, while actuator 114 is held by a thumb of the same hand. A stop 120 may extend into lumen 116 from an inner circumferential surface of body 112.

Links 108 and distal tip 110 may be formed from any suitable material, such as, e.g., a metal, a metal alloy (stainless steel, nitinol, or the like), or a polymer. Each link 108 and distal tip 110 may include a lumen extending therethrough. Distal tip 110 also may include a needle tip at its distal end having any suitable shape, such as, e.g., a bevel tip (as shown in FIGS. 1 and 2), multiple bevels, conical, Sprotte, diamond, Franseen, Tuohy, or the like or any other suitable needle tip shape. In the rigid configuration, links 108 and distal tip 110 form needle 109 suitable for injecting fluids, performing aspiration, collecting biopsy samples, and any other suitable technique that utilizes needles. Any suitable number of links 108 may be used, including, but not limited to one, two, three, four, eight, or more links 108.

A conduit 122 may extend from proximal end 102 toward distal end 104. Conduit 122 may be fixed or otherwise coupled to actuator 114 at proximal end 102, and to distal tip 110 at distal end 104 by any suitable mechanism, such as, e.g., snap-fitting, mechanical fasteners, biocompatible adhesives or the like. One or more of links 108 may loosely ride along conduit 122 in the loose configuration. Conduit 122 may include a lumen 124 extending therethrough, and a stop 130 disposed on an outer circumferential surface of conduit 122. Stop 130 may be distal to stop 120. Conduit 122 may be formed from any suitable fluid-impermeable material including, e.g., metals, polymers and the like. Conduit 122 may be biased into a straight configuration (shown in FIGS. 1 and 2), but may be configured to flex in order to navigate through tortuous anatomy. However, after flexing, conduit 122 may return to the straight configuration shown in FIGS. 1 and 2. Further, conduit 122 may be sufficiently rigid to compress a spring 132 when medical device 100 is transitioned from the loose configuration to the rigid configuration. Spring 132 may be disposed between stop 120 of handle 106, and stop 130 of conduit 122.

Lumen 124 of conduit 122 may permit fluid and/or tissue flow through needle 109 while needle 109 is in any configuration, including the floppy, loose configuration of FIG. 1, and the rigid configuration of FIG. 2. In the absence of conduit 122, fluid and/or tissue travelling through needle 109 may escape needle 109 through gaps between adjacent links 108. Even in the rigid configuration, small gaps due to manufacturing imperfections may be present between adjacent links 108, making needle 109 unsuitable for biopsy or fluid delivery in the absence of conduit 122. In other aspects, however, needle 109 may be fluid tight in the absence of conduit 122 while in the rigid configuration. Fluid delivery and/or aspiration devices may be coupled to a proximal end of conduit 122 to enable sample collection, irrigation, and/or spraying of a target site. Conduit 122 may include a plurality of lumens in order to carry out one or more of these functions sequentially or simultaneously.

The loose configuration (FIG. 1) may help medical device 100 navigate through tortuous pathways of the body, or to navigate through the tortuous path of an artificial lumen of a scope extended through a tortuous pathway of the body. Medical device 100 also may be used to deflect tissue or other bodily structures while disposed in its rigid, compact state (FIG. 2).

In the loose configuration, the various links 108 may be spaced apart from adjacent links 108, and may loosely ride along conduit 122. The distalmost link 108 also may be spaced apart from distal tip 110 in the loose configuration. However, in the rigid configuration, the links 108 of the medical device 100 may directly contact one another in a nested manner, and the distalmost link 108 may contact distal tip 110 in a nested manner. In the loose configuration, the links 108 and distal tip 110 of medical device 100 may change orientation relative to one another in response to an outside force acting on one or more of the links 108 or on the distal tip 110. In the rigid configuration, the links 108 and distal tip 110 of medical device 100 may not change orientation relative to one another in response to an outside force (such as the same outside force (magnitude and direction) mentioned in the prior sentence) acting on one or more of the links 108 or distal tip 110. That is, in the rigid configuration, the links 108 and distal tip 110 may form a rigid member that is substantially straight, and which remains substantially straight when contacting tissue or other objects. Thus, distal end 104 of medical device 100 comprising the plurality of links 108 and the distal tip 110 may have a greater rigidity in the rigid configuration than while in the loose configuration. Additionally, the plurality of links 108 and the distal tip 110 may be fixed relative to one another when in the rigid configuration, and may be movable relative to one another in the loose configuration. Needle 900 (measured from a distal end of handle 106) also may have a greater length in the loose configuration than when in the rigid configuration, as gaps between adjacent links 108 and/or distal tip 110 present in the loose configuration may be closed after the transition to the rigid configuration.

The movement of actuator 114 relative to body 112 may be configured to transition medical device 100 between the loose and rigid configurations. When medical device 100 is in the loose configuration of FIG. 1, a proximally directed force may be applied by actuator 114 to conduit 122. Further, because distal tip 110 is fixed to conduit 122, the proximal movement of conduit 122 also causes proximal movement of distal tip 110. Distal tip 110 then may abut a distalmost link of the plurality of links 108, closing off a gap that existed between distal tip 110 and the distalmost link 108 in the loose configuration. The distalmost link 108 then may abut a link 108 immediately proximal to the distalmost link, and this pattern may be repeated until the gaps between each adjacent link 108 have been closed. Thus, in response to the proximally directed force, medical device 100 may move from the loose configuration of FIG. 1 to the rigid configuration of FIG. 2 by compressing spring 132 and causing a gap between distal tip 110 and distalmost link 108, and gaps between other adjacent links of the plurality of links 108, to close. In some aspects, the proximally directed force must be maintained to keep medical device 100 in the rigid configuration, although a locking device (not shown) could be used to keep medical device in the rigid configuration. Medical device 100 may be transitioned back to the loose configuration by releasing the proximally directed force acting on conduit 122, allowing spring 132 to expand longitudinally and force the links 108 and distal tip 110 of medical device 100 away from one another. The links 108 and distal tip 110 may be slack and floppy in the loose configuration. One or more springs (not shown) may be disposed between adjacent links to bias the adjacent links apart from one another.

Figure 4:
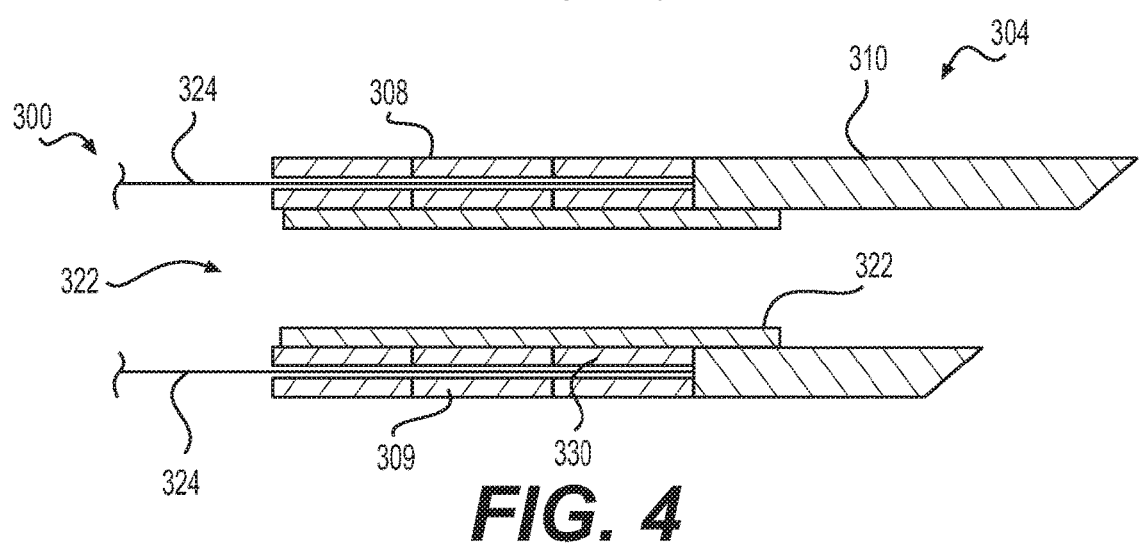
FIG. 4 is a side cross-sectional view of the medical device of FIG. 3 in a second configuration.

A medical device 300 is shown in a first, loose configuration in FIG. 3, and in a second, rigid configuration in FIG. 4. Medical device 300 may be reciprocally movable between the first and second configurations like medical device 100, except that medical device 300 may utilize one or more actuation members 324 instead of conduit 122 to carry out the reciprocal movement between the two configurations. Medical device 300 may extend from a proximal end (not shown) toward a distal end 304. Medical device 300 may include a handle (not shown) at the proximal end, a plurality of links 308, and a distal tip 310. The plurality of links 308 and the distal tip 310 may form a needle 309 when medical device 300 is in the second configuration of FIG. 4. Medical device 300 may have substantially similar elasticity, rigidity, and other properties, in the loose and rigid configurations as described above with respect to medical device 100.

Links 308 may be substantially similar to links 108 described above, except that links 308 also may include one or more actuation lumens 326. In the aspect shown in FIGS. 3 and 4, each link 308 includes two actuation lumens 326 that are diametrically opposed from one another (e.g., are separated by an arc length of 180 degrees). However, it is also contemplated that other suitable numbers of actuation lumens and/or spacing may be utilized. Each link 308 also may include a fluid lumen 328 extending through a center of the link 308. The actuation lumens 326 of the links 308 may be aligned with one another to form actuation lumens 330, and fluid lumens 328 may be aligned with one another to form a fluid lumen 332, when medical device 300 is in the rigid configuration. Distal tip 310 may be substantially similar to distal tip 110 described above with reference to FIGS. 1 and 2.

Actuation members 324 may extend through each of the actuation lumens 330 (and 326), and may be coupled at their proximal ends to an actuating mechanism and/or handle. The distal ends of actuation members 324 may be coupled to a proximally-facing surface of distal tip 310. Actuation members 324 may be wires, cables, rods, tubes, or any other suitable members configured to receive a proximally directed pulling force from the actuating mechanism. The actuating mechanism may include any suitable features configured to apply the proximally directed pulling force to actuation members 324, including, for aspect, one or more of gears, pulleys, wheels, shafts, and the like. Actuating mechanism 124 may be motorized and/or electrically driven in some aspects, and/or may be actuated manually by the operator.

Medical device 300 may include a sleeve 322 that extends through needle 309 from the proximal end to distal end 304. Sleeve 322 may be formed from a polymer material, such as, e.g., an elastomeric polymeric material. Aspects of polymers that could be used to form sleeve 322 include Teflon®, PTFE, FEP, polyethylene and polypropylene, silicone, polyurethane and polyether-block-amide, among others. Sleeve 322 may be a flexible, floppy, compliant, and/or impermeable membrane. That is, sleeve 322 may have a sheet-like structure configured to collapse upon itself when no outside forces are applied to the sleeve 322. In some aspects, sleeve 322 may include an elastic and/or resilient material. Sleeve 322 may be a long and flexible rubber tubing.

Figure 5:
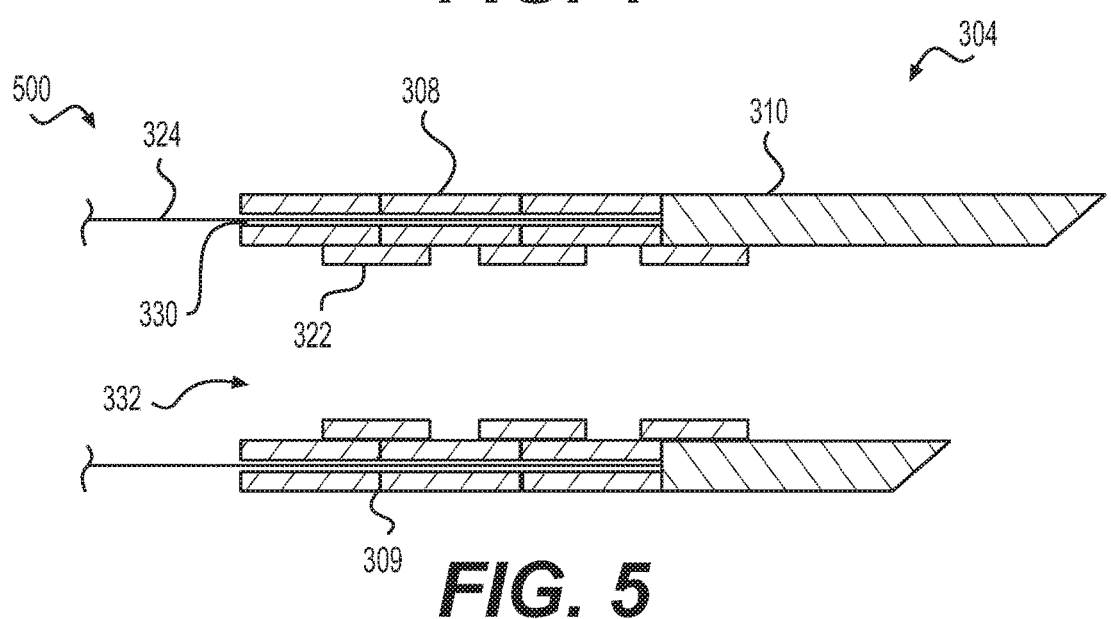
FIG. 5 is a side cross-sectional view of a medical device according to another aspect of the present disclosure.

A medical device 500 is shown in FIG. 5 that is substantially similar to medical device 300, except that instead of a single sleeve 322, multiple seals 522 are utilized to facilitate fluid flow through medical device 500. That is, a seal 522, which may be formed from substantially similar materials as sleeve 322, may be coupled to inner surfaces of adjacent links 308, and to inner surfaces of a distalmost link 308 and distal tip 310 to form an airtight and fluid-tight seal. Seals 522 may be configured to stretch in an axial direction to enable the needle to obtain the loose configuration (not shown). In another aspect, seals 522 may be disposed longitudinally between adjacent links 308, and longitudinally between distalmost link 308 and distal tip 310. In this aspect, seals 522 may be annular O-rings or gaskets. The gasket may be formed of an elastomeric material that is somewhat compressible in order to allow the gasket to provide a substantially airtight and fluid seal between adjacent links 308 or between distalmost link 308 and distal tip 310. In other aspects a sealing coating may be applied to inner and/or end surfaces of links 308.

Figure 6:
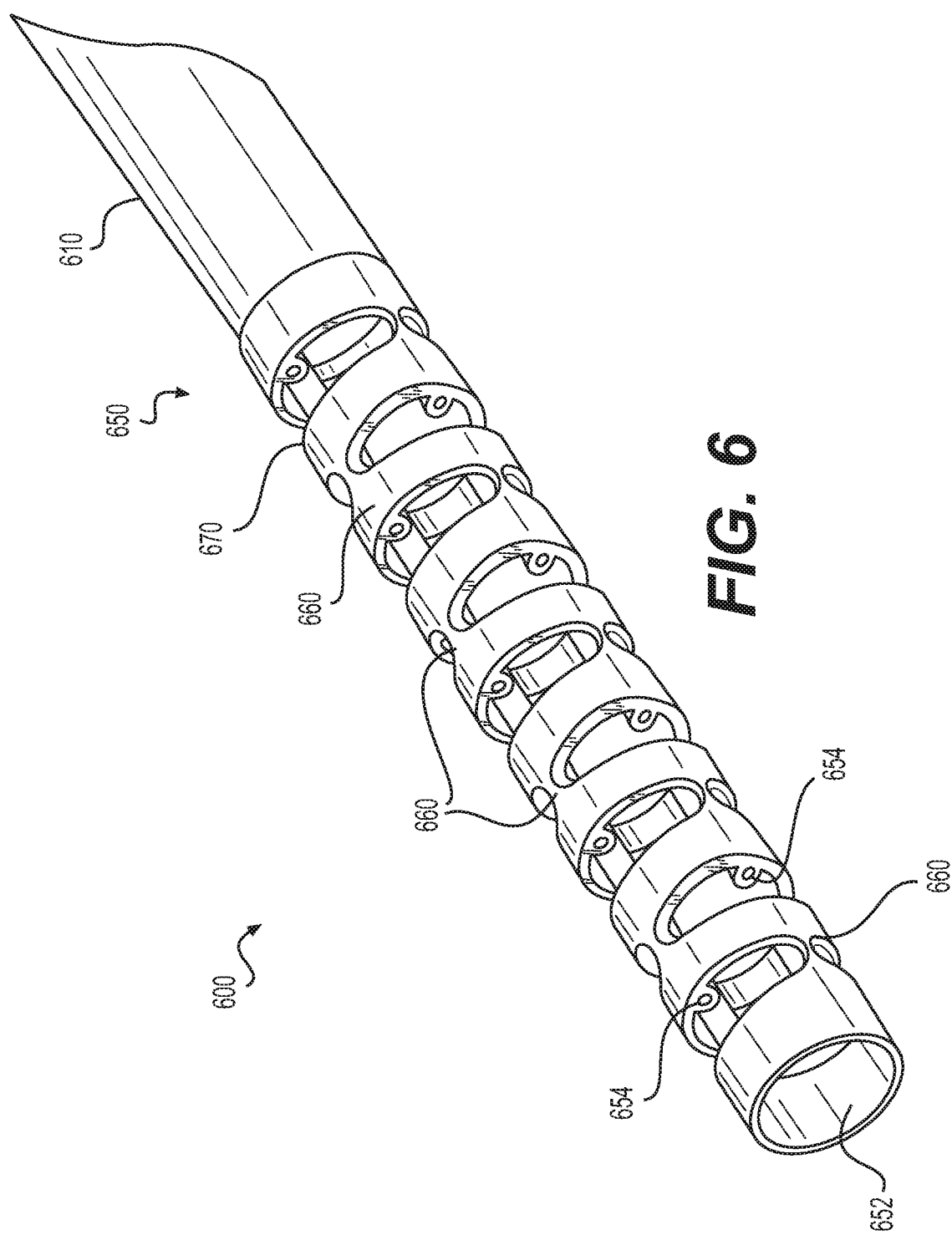
FIG. 6 is a perspective view of a needle, according to another aspect of the present disclosure.

A needle 600 is shown in FIG. 6 having an articulation joint 650. The articulation joint 650 may allow needle 600 to be turned back on itself, e.g., over an arc of 180 degrees. Articulation joint 650 may be generally cylindrical in shape and may include a central lumen 652, and one or more actuation lumens 654 located in the walls of the articulation joint 650. Three actuation lumens 654 are in each joint 650, and are arranged 120 degrees apart from one another. However, other suitable numbers of actuation lumens may alternatively be utilized.

One or more living hinges 660 may be formed along a length of articulation joint 650 to facilitate bending of articulation joint 650. Each living hinge 660 may include a pair of opposing V-shaped cuts 670 on either side of the articulation joint 650. The cuts 670 may extend circumferentially around the articulation joint. Longitudinally adjacent living hinges 660 may be circumferentially offset from one another by 90 degrees.

The articulation joint can be formed by extruding a cylinder with the central and actuation lumens in place and cutting the cylinder tube with a knife, laser, milling tool, water jet, or other material removal mechanism to form the living hinges. Alternatively, articulation joint 650 can be molded with the living hinge joints in place. The angles of the V-shaped cuts 670 that form the hinges may be uniform or may vary along the length of the articulation joint 650. Similarly, the distance between adjacent living hinges 660 may be uniform or may vary in order to tailor the bending and torque characteristics of the articulation joint 650. In one aspect, each living hinge 660 has a closing angle of 30 degrees so that six hinges are required to provide 180 degrees of movement. Actuation lumens 654 may be aligned with the widest spacing of the living hinges 660. However, it may be desirable to offset the actuation lumens 654 with respect to the hinges in order to lessen potential binding of the actuation members in the hinge. Articulation joint 650 may include a biocompatible material that will bend but will not collapse. Suitable materials include polyurethane, polyethylene, polypropylene, or other biocompatible polymers. In another aspect, articulation joint 650 may be formed by 3D-printing or other additive manufacturing techniques.

A distal tip 610 that is substantially similar to distal tip 110 may be positioned at the distal end of articulation joint 650. Additionally, a sleeve that is substantially similar to sleeve 322 may extend through needle 600 to facilitate fluid flow through needle 600. Thus, in some aspects, fluid and/or tissue acquired during a biopsy with needle 600 must travel through sleeve 322. Distal tip 610 may be sufficiently long such that no portion of articulation joint 650 needs to be inserted through tissue during acquisition of biopsy samples. In other aspects, articulation joint 650 may be inserted through tissue during sample acquisition.

Referring to FIGS. 7A and 7B, a needle 700 (shown in FIG. 7B) is made of a series of stacked links 750 that are positioned adjacent one another and that move with respect to one another. As shown in FIG. 7A, a link 750 may include an annular ring 752 having a pair of distal facing rocker surfaces or cams 754, and a pair of proximal facing rocker surfaces or cams 756. The distal facing cams 754 may be positioned 180 degrees apart on the distal surface of the annular ring 752, while the proximal facing cams 756 may be positioned 180 degrees apart on the proximal face of the annular ring 752. In the aspect shown, the proximal facing cams 756 may be oriented at 90 degrees with respect to the distal facing cams 754. Each cam 754 or 756 may engage and rock against a flat section of an adjacent link 750. Holes 760 are drilled through the annular ring and through the cams 754 and 756 for passage of actuation members. Upon tension of the actuation members, the links 750 will rock on the surface of the cams 754, 756, thereby bending the needle 700 in the desired direction. Distal facing cams 754 may be aligned with other distal facing cams 754, and proximal facing cams 756 may be aligned with other proximal facing cams 756 when needle 700 is assembled. A distal tip 710 that is substantially similar to distal tip 110 may be positioned at the distal end of needle 700. Additionally, a sleeve that is substantially similar to sleeve 322 may extend through needle 700 to facilitate fluid flow through needle 700.

FIG. 8A shows a link 880, and FIG. 8B shows a needle 800 including a series of stacked links 880. Each link 880 may include an annular ring having a pair of concave pockets 882 on its proximal surface, and a pair of correspondingly shaped convex cams 884 on its distal surface. On a given link 880, concave pockets 882 may be offset by 90 degrees with respect to the convex cams 884. However, the concave pocket 882 of a given link may be aligned with and receive a convex cam 884 of an adjacent link. The correspondingly shaped cams 884 and pockets 882 help prevent the stacked links 880 from rotating with respect to one another. Holes or lumens 886 are formed through the link 880 for passage of one or more actuation members 890. The holes or lumens 886 may be positioned at the center of the cams and pockets. However, the holes for the actuation members may be offset from the position of the cams and pockets, if desired. Links 880 may be molded from a biocompatible polymer having a relatively slick surface, such as polyurethane, polypropylene, or polyethylene, which reduces friction between adjacent cams and pockets. A distal tip 810 that is substantially similar to distal tip 110 may be positioned at the distal end of needle 800. Additionally, a sleeve that is substantially similar to sleeve 322 may extend through needle 800 to facilitate fluid flow through needle 800.

FIGS. 9A and 9B show a needle 900 including a series of stacked links 980 and 981, each comprising an annular ring having at least one pocket 982 on its proximal surface and at least one correspondingly shaped cam 984 on its distal surface. Links 981 may include an additional cam 985 that extends from the distal surface of link 981, and that is circumferentially offset from cam 984. Cam 985 may not be aligned with any corresponding pocket of an adjacent link, and instead may engage and rock with a flat section of a proximal surface of a distally-adjacent link 980 or 981. The cams 985 of adjacent links 981 may be disposed on diametrically opposed sides in some aspects, as shown in FIGS. 9A and 9B. Alternatively, the cams 985 of adjacent links 981 may be disposed on the same side of needle 900, for aspect, to create a larger curvature in the needle 900. Cams 985 may drive the length and angle of the articulating section of the needle 900. Lengthening cams 985 may allow for a longer length of needle 900, and increase the angle that the needle 900 is able to achieve. Positioning various cams 985 in different planes could also allow for the articulating section to take on different shapes other than one radial curve, such as, e.g., an S-curve.

Adjacent links 980 may be fully nesting such that no gap exists between adjacent links 980 when in a rigid configuration (shown in FIG. 9B). Links 981, however, may be only partially-nesting or may not nest at all with an adjacent link 980 or 981. The combination of fully-nesting and non-nesting links may enable needle 900 to have certain portions with high rigidity in the rigid configuration, and other portions that can provide the ability to change the shape and direction of needle 900. The needle 900 may be transitioned between a loose configuration (shown in FIG. 9A) and the rigid configuration by actuation of actuation members 924 in a substantially similar manner as set forth above with respect to medical device 300 described with reference to FIGS. 3 and 4. A distal tip 910 that is substantially to distal tip 110 may be positioned at the distal end of needle 900. Additionally, a sleeve that is substantially similar to sleeve 322 may extend through needle 900 to facilitate fluid flow through needle 900.

Figure 10:
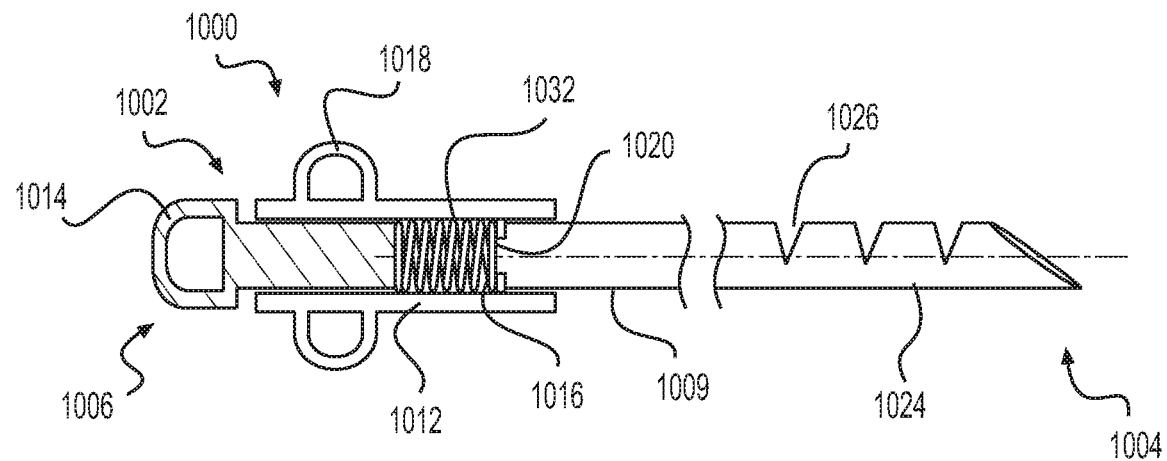
FIG. 10 is a side cross-sectional view of a medical device in a first configuration, according to an aspect of the present disclosure.
Figure 11:
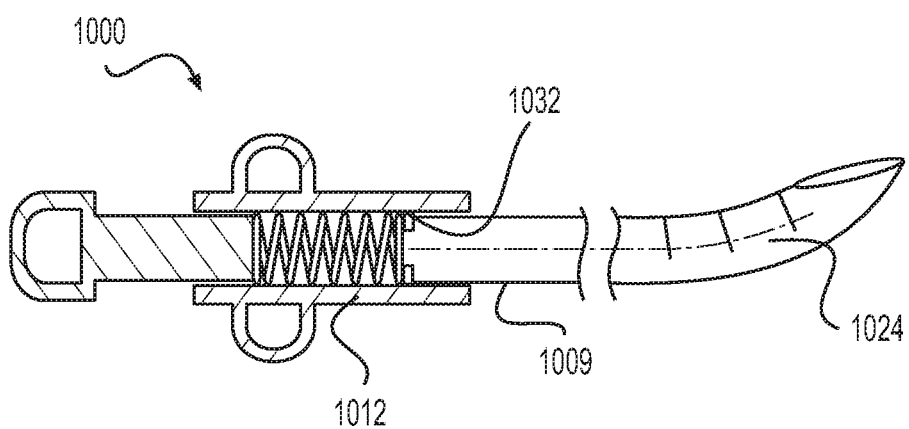
FIG. 11 is a side cross-sectional view of the medical device of FIG. 10 in a second configuration.

A medical device 1000 is shown in a first, flexible configuration in FIG. 10, and in a second, rigid configuration in FIG. 11. Medical device 1000 may be reciprocally movable between the first and second configurations, and also may be configured to extend through an endoscopic device. Medical device 1000 may extend from a proximal end 1002 toward a distal end 1004. Medical device 1000 may include a handle 1006 at proximal end 1002, and a needle 1009 extending distally from handle 1006.

Handle 1006 may include a body 1012, and an actuator 1014 that is slidable or otherwise movable relative to body 1012. Body 1012 may include a lumen 1016, and two diametrically opposed grips 1018. Handle 1006 may be substantially similar to handle 106 described with reference to FIGS. 1 and 2. A stop 1020 may extend into lumen 1016 from an inner circumferential surface of body 1012.

Needle 1009 may be formed from any suitable material, such as, e.g., a metal, a metal alloy (stainless steel, nitinol, or the like), or a polymer. The distal end of needle 1009 also may include a needle tip having any suitable shape, such as, e.g., a bevel tip, multiple bevels, conical, Sprotte, diamond, Franseen, Tuohy, or the like or any other suitable needle tip shape. In the rigid configuration, needle 1009 may be suitable for injecting fluids, aspirating, collecting biopsy samples, and any other suitable technique that utilizes needles. Needle 1009 may include one or more notches 1026 that are positioned on the same side of needle 1009.

An actuation member 1024 may extend distally from actuator 1014, and may be coupled to distal end 1004 of needle 1009. In one aspect, medical device 1000 includes only one actuation member, although other suitable actuation members could also be used. A spring 1032 may be disposed between stop 1020 of handle 1006, and actuator 1014. Spring 1032 is longitudinally compressed in the flexible configuration of FIG. 10, and is longitudinally extended to a resting configuration when medical device 1000 is in the rigid configuration of FIG. 11.

The movement of actuator 1014 and actuating member 1024 relative to body 1012 may be configured to transition medical device 1000 between the loose and rigid configurations. As set forth above, spring 1032 is longitudinally-compressed in the loose configuration. Actuating member 1024 is slack in the same configuration of medical device 1000. When medical device 1000 is in the loose configuration of FIG. 10, a distally-directed force on actuator 1014 may be released, causing actuator 1014 to move proximally, allowing spring 1032 to extend into the resting position shown in FIG. 11. The proximal movement of actuator 1014 may increase tension in actuating member 1024 until actuating member 1024 becomes taut. This may cause the distal end of the needle 1009, which is coupled to actuating member 1024, to flex away from a longitudinal axis of medical device 1000, and forcing closure of notches 1026. The flexed configuration of needle 1009 may include a radius of curvature such that needle 109 resembles an arc. Medical device 100 may be transitioned back to the loose configuration by reapplying a distally directed force acting on actuator 1014, compressing spring 1032. This compression causes actuation member 1024 to move from the taut configuration to the slack configuration, causing notches 1026 to reappear, and reverting needle 1009 to the loose configuration of FIG. 10.

An operator may be required to maintain a distally-directed force on actuator 1014 in order to navigate needle 1009 through tortuous anatomy. Then, when needle 1009 is advanced outside of an introducing device, e.g., an endoscope, the operator may release the distally-directed force, and perform a biopsy procedure with the needle 1009.

Figure 12:
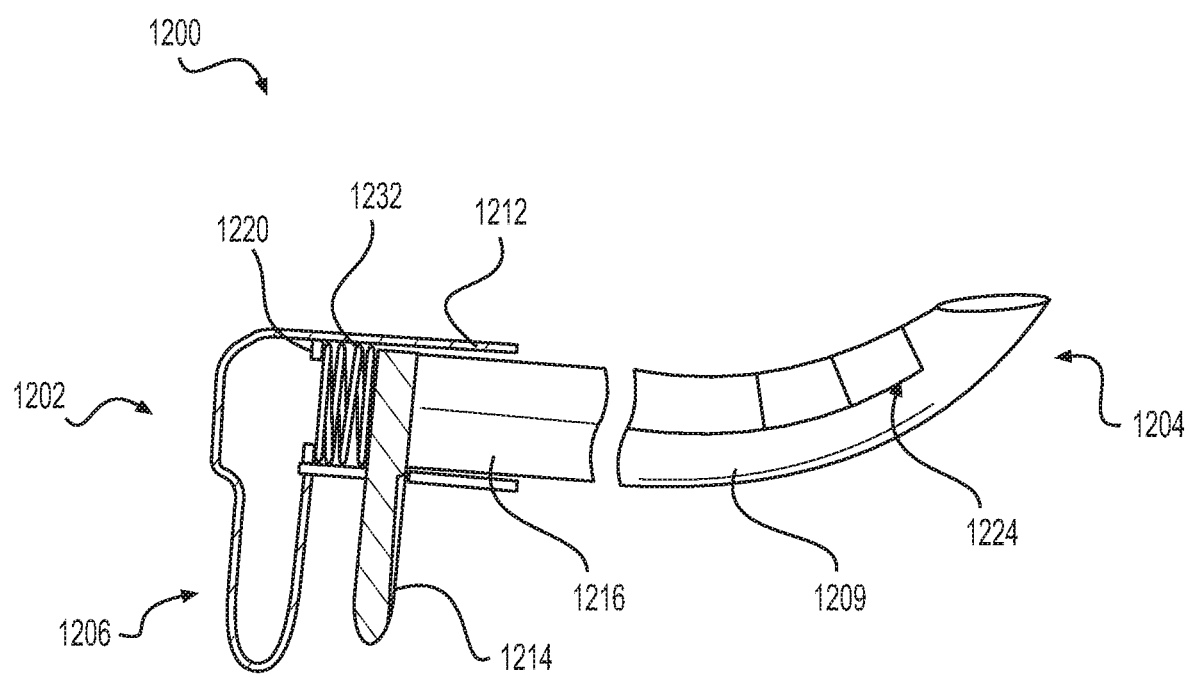
FIG. 12 is a side cross-sectional view of a medical device according to another aspect of the present disclosure.

A medical device 1200 is shown in FIG. 12. Medical device 1200 is reciprocally movable between a first, flexible configuration (not shown), and a second, rigid configuration shown in FIG. 12. Medical device 1200 may extend from a proximal end 1202 toward a distal end 1204. Medical device 1200 may include a handle 1206 at proximal end 1202, a needle 1209 extending distally from handle 1206, and an actuating member 1224. Needle 1209 and actuating member 1224 may be substantially similar to needle 1009 and actuating member 1024 described with reference to FIGS. 10 and 11.

Handle 1206 may include a body 1212, and an actuator 1214 that is slidable or otherwise movable relative to body 1212. Body 1212 may include a lumen 1216. A stop 1220 may extend into lumen 1216 from an inner circumferential surface of body 1212. Actuator 1214 may be disposed distally of stop 1220.

Actuation member 1224 may extend distally from actuator 1214, and may be coupled to distal end 1204 of needle 1209. A spring 1232 may be disposed between stop 1220 of handle 1206, and a proximally-facing surface of actuator 1214. Spring 1232 is longitudinally-extended in a resting position while medical device 1200 is in the flexible configuration (not shown), and is longitudinally-compressed in the rigid configuration of FIG. 12.

The movement of actuator 1214 and actuating member 1224 relative to body 1212 may be configured to transition medical device 1200 between the loose and rigid configurations. As set forth above, spring 1232 is longitudinally-extended in the loose configuration of medical device 1200. When medical device 1200 is in the loose configuration, a proximally-directed force may be applied to actuator 1214, causing actuator 1214 to move proximally, compressing spring 1232. The proximal movement of actuator 1214 may cause the distal end of the needle 1209, which is coupled to actuating member 1224, to flex away from a longitudinal axis of medical device 1200, and to force closure of the notches of needle 1209. Needle 1209 may have a radius of curvature and may otherwise resemble an arc in this configuration. Thus, in response to the proximally directed force, medical device 1200 may move from the loose configuration, to the rigid configuration of FIG. 12 by compressing spring 1232. In some aspects, the proximally-directed force must be maintained to keep medical device 1200 in the rigid configuration. Medical device 1200 may be transitioned back to the loose configuration by releasing the proximally directed force acting on actuation member 1224 and actuator 1214, allowing spring 1232 to expand longitudinally, causing the notches to reappear, and reverting needle 1209 to a loose configuration similar to the configuration shown in FIG. 10.

Medical device 1200 may be configured such that no additional force needs to be applied in order to navigate medical device 1200 through tortuous anatomy (other than the force required to move the medical device 1200 itself). Instead, once medical device 1200 is positioned adjacent a working site, a proximally-directed force may be applied to actuator 1214 to transition needle 1209 to the rigid configuration suitable for collecting biopsy samples.

Figure 13:
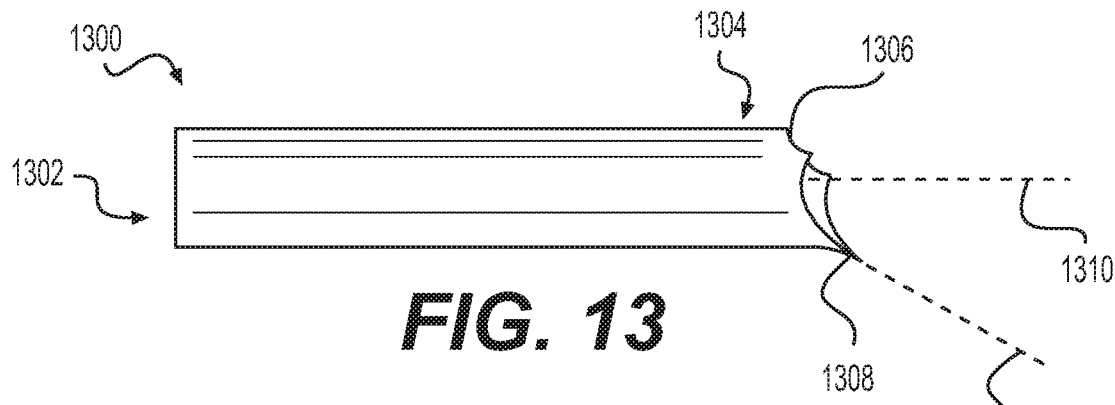
FIG. 13 is a side view of a needle according to an aspect of the present disclosure.

A needle 1300 is shown in FIG. 13. Needle 1300 may extend from a proximal end 1302 toward a distal end 1304. Needle 1300 may be substantially similar to any of the needles described herein, and also may include a distal point 1308 that is splayed radially outward from a distal tip 1306 of needle 1300. The distal point 1308 may be a distalmost point of a path travelling along an entirety of needle 1300. Distal point 1308 also may be a permanent portion of needle 1300 that is present in every configuration of the needle 1300, as opposed to being present in only some configurations of needle 1300. Thus, as needle 1300 travels along tortuous anatomy, curves, expands, or compresses, distal point 1308 may remain unchanged relative to a remainder of distal tip 1306. Distal point 1308 may be the first portion of needle 1300 that pierces through tissue, and its radially outward orientation may cause a remainder of needle 1300 to follow a path 1311 through tissue that is offset from a central longitudinal axis 1310 of needle 1300. That is, after distal point 1308 pierces through tissue and in response to a force directed along central longitudinal axis 1310, needle 1300 may flex and follow path 1311 through tissue.

Figure 14:
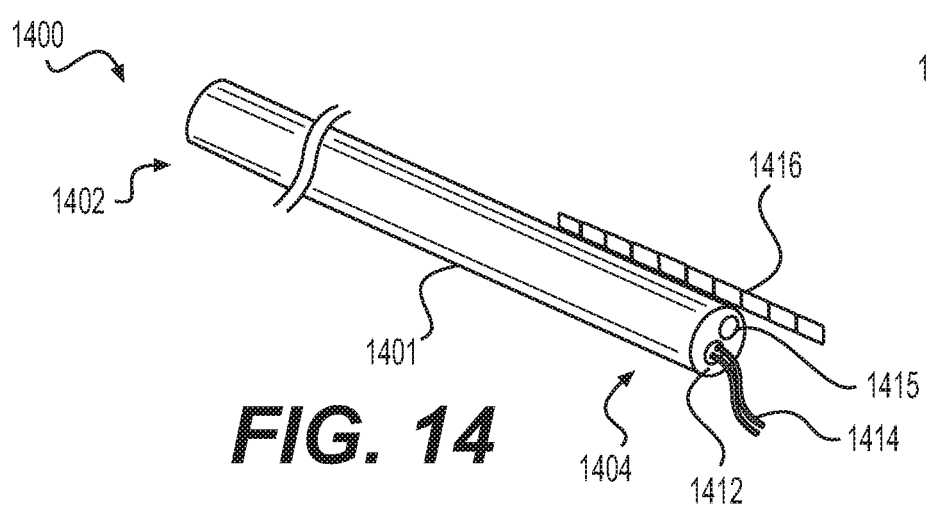
FIG. 14 is a perspective view of a medical device according to another aspect of the present disclosure.

A scope 1400 is shown in FIG. 14. Scope 1400 may include a flexible shaft 1401 that extends from a proximal end 1402 to a distal end 1404. Shaft 1401 may be configured to navigate tortuous anatomy within a patient. In some aspects, shaft 1401 may be uniformly flexible, or may include portions having varied flexibility. For aspect, distal end 1404 of shaft 1401 may be more flexible than proximal end 1402. Scope 1400 may be any suitable medical scope, such as, e.g., an endoscope, a ureteroscope, a colonoscope, a hysteroscope, a bronchoscope, or a cystoscope. Shaft 1401 may be directly inserted into the body of a patient or may be extended over a guidewire using one or more lumens. Shaft 1401 also may be inserted into a laparoscopic port, a single incision port, an over-tube, a bouché, or any other suitable member.

Shaft 1401 may include a single lumen 1412 (e.g., only one lumen), although any other suitable number of lumens may be utilized. For aspect, an additional lumen 1415 may be configured to accommodate any suitable visual device. For aspect, a lumen 1415 may be configured to contain a visual device allowing a user to view an area adjacent to distal end 1404 of scope 1400, including areas distal to distal end 1404. The visual device may be built into scope 1400, and include one or more of a light source, lens, fiber optics, and/or any suitable electronic vision components known in the art, etc., to view a work site within a patient's body lumen. In another aspect, a separate imaging device may be utilized. It is also contemplated further additional lumens (not shown) may be utilized for any other suitable purpose, such as, e.g., irrigation, aspiration, suction, delivery of additional tools, delivery of therapeutics, or as a guiding lumen which is used to guide shaft 1401 over a guidewire.

A tool 1414 may extend through lumen 1412. Tool 1414 may include a cutting knife, a cutting wire, an injection needle, a needle knife, a snare, or other therapeutic or diagnostic devices, including any of the devices set forth herein.

A deflecting tool 1416 may be coupled to an outer surface of shaft 1401. Deflecting tool 1416 may be substantially similar to any of the medical devices and/or needles described herein that are movable between a loose configuration and a rigid configuration. However, in some aspects, deflecting tool 1416 may have a blunt, atraumatic distal tip, instead of a sharp distal tip. The atraumatic tip may be configured to reduce or prevent damage to tissue that is contacted by the atraumatic tip. For aspect, the atraumatic tip may include a polymer material having a relatively small durometer or hardness. In other aspects, the atraumatic tip may include a ball tip or any other features, such as rounded edges, configured to reduce damage to tissue that contacts the tip.

Deflecting tool 1416 may be used to deflect tissue or other bodily structures while disposed in the rigid configuration, and may be used to hold and position tissue prior to and during manipulation or resection. For aspect, deflecting tool 1416 may be placed adjacent to or in contact with tissue to be resected or biopsied, and transitioned to the rigid state to push or deflect the tissue to an optimal cutting position. In some aspects, the deflecting tool can be used to make target tissue taut to facilitate cutting of the target tissue.

Figure 15:
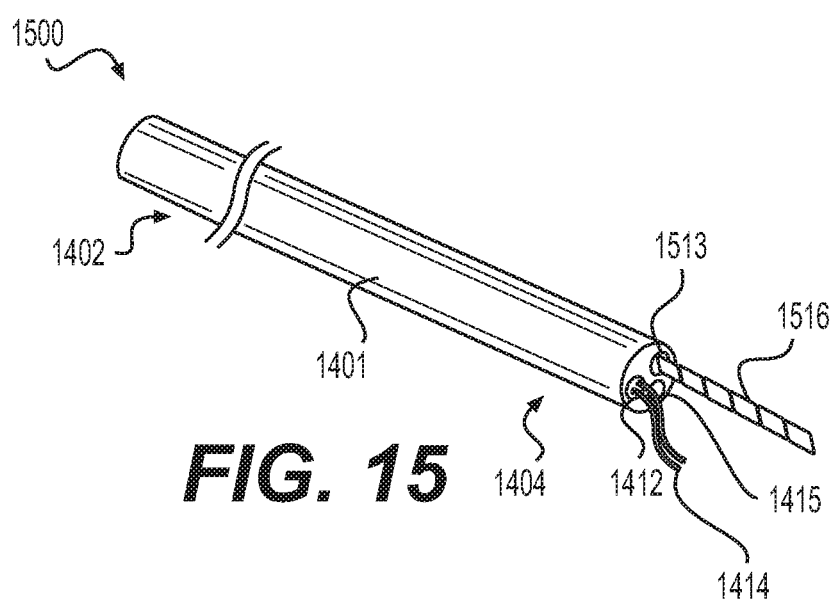
FIG. 15 is a perspective view of a medical device according to another aspect of the present disclosure.

A scope 1500 is shown in FIG. 15 that is substantially similar to scope 1400, except that scope 1500 may include at least one additional lumen 1513. A deflecting tool 1516 may extend through additional lumen 1513. The deflecting tool 1516 may be substantially similar to deflecting tool 1416 and may be used in a substantially similar manner. The opening of lumen 1513 at the distal end of scope 1500 may lie in a plane, and deflecting tool 1516 may be configured to extend distally away from the distal end 1504 along a trajectory that is substantially perpendicular to the plane of the opening.

Articulating needles of the present disclosure may include only two configurations in some aspects. For aspect, the two configurations of a needle may be offset from one another by 45 degrees. In other aspects, articulating needles may be continuously variable with the use of back tension springs or incompletely cut links, which would allow the needles to spring back to an initial shape when no tension is applied by the user.

One or more portions of the disclosed medical devices and needles may include a lubricious coating to reduce friction between the medical devices or needles, and contacted tissue. Any suitable lubricious coating may be utilized, including water soluble, biocompatible compounds that impart lubricity to the surface of otherwise non-lubricious materials. One class of hydrophilic coatings includes hydrogels, which swell in an aqueous environment, and are capable of manifesting lubricity while in a wet or hydrated state. When hydrated, these substances have low frictional forces in humoral fluids including saliva, digestive fluids and blood, as well as in saline solution and water. Hydrogels include polyethylene oxides, optionally linked to the substrate surface by urethane or ureido linkages or interpolymerized with poly(meth)acrylate polymers or copolymers, copolymers of maleic anhydride, (meth)acryl amide polymers and copolymers, (meth)acrylic acid copolymers, polyurethanes, poly(vinyl pyrrolidone) and blends or interpolymers with polyurethanes, polysaccharides, and mixtures thereof.

Medical devices of the present disclosure also may be coated with an antibacterial covering to inhibit bacterial growth on its surface. The antibiotic coating may contain an inorganic antibiotic agent, disposed in a polymeric matrix that adheres the antibiotic agent to a device surface. Further, a drug-releasing coating may also be applied to the device surface, assisting in delivery of drugs to the biopsy site. In another alternative, imaging markers may be applied to various medical devices, to assist in locating the medical devices within the body. Radiopaque, sonoreflective, and/or any other suitable markers may be employed.

Figure 16:
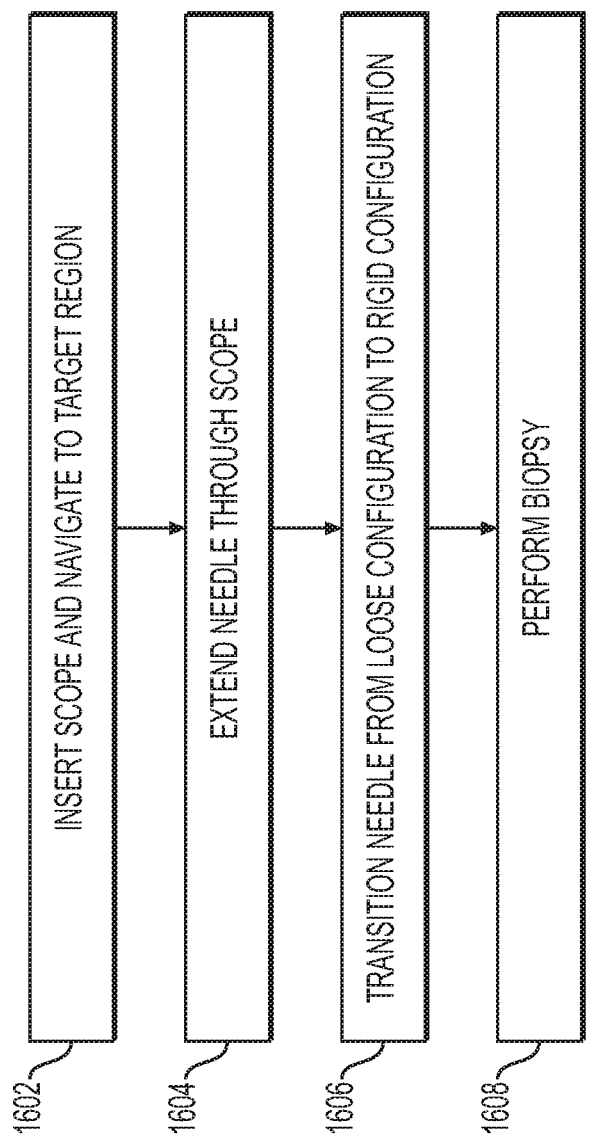
FIG. 16 is a flowchart of a method according to an aspect of the present disclosure.

A method 1600 is shown in FIG. 16. The method 1600 may begin at step 1602, where an endoscope or other suitable member may be inserted into the body and navigated to a target region. For aspect, an endoscope may be inserted into the body through a natural anatomic opening, such as, for aspect, the mouth, anus, nose, or vagina. Alternatively, the endoscope may be inserted into the body through an incision. An operator may navigate the endoscope from the point of insertion to a target region (e.g., work site) within the body by traversing a body channel, such as, e.g., the biliary system. In other aspects, the work site may include a lymph node or any other tissue that may be potentially cancerous and has been identified for biopsy and further study.

Once a distal end of the endoscope is adjacent or otherwise proximate to the target region, a needle according to any of the aspects of the present disclosure may be inserted through a port of the endoscope while in a loose configuration at step 1604. The floppy needle then may be pushed toward the distal end of the endoscope. Once the needle exits the distal end of the endoscope, the method may proceed to step 1606, where the needle may be transitioned from the loose configuration to a rigid configuration. Once the needle is in the rigid configuration, it may be extended further distally from the scope to pierce tissue and collect a sample at step 1608. Step 1608 may be repeated numerous times around and/or through the same target area (e.g., an eccentric lesion) in order to acquire tissue samples from multiple portions of the target area (e.g., fanning). The multiple samples may be taken while keeping the introducing endoscope in a fixed position, which may result in a significant reduction in procedure time.

Figure 17:
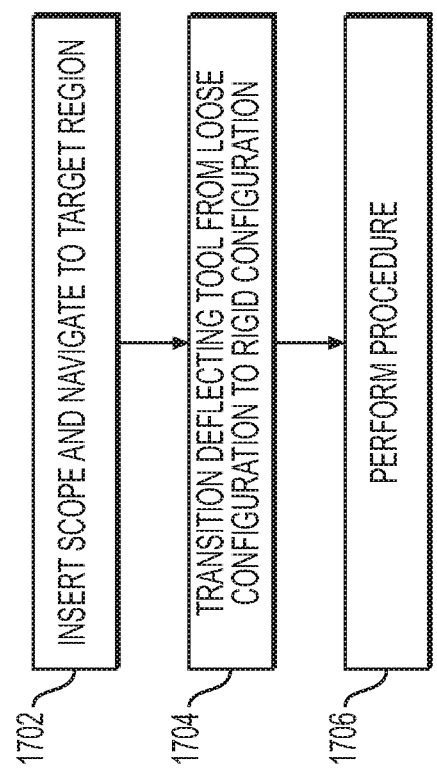
FIG. 17 is a flowchart of a method according to another aspect of the present disclosure.

A method 1700 is shown in FIG. 17. Step 1702 may be substantially similar to step 1602 of method 1600, except that scope 1400 or 1500 may be used instead of the endoscope described with reference to method 1600. Once scope 1400 or 1500 is positioned adjacent to a target or otherwise proximate to the target region, deflection tool 1416 or 1516 may be transitioned from a loose configuration to a rigid configuration to prepare tissue for manipulation, cutting, or resection at step 1704. Once the tissue is ready, the subsequent procedure (e.g., cutting) may be performed at step 1706 by tool 1414.

Those skilled in the art will understand that the medical devices set out above can be implemented in any suitable body lumen (e.g., blood vessels, the biliary tract, urological tract, gastrointestinal lumens, and the like) without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other aspects of the present disclosure will be apparent to those skilled in the art from consideration of the specification and practice of the aspects disclosed herein. It is intended that the specification and aspects be considered as implementations only, and departures in form and detail may be made without departing from the scope and spirit of the present disclosure as defined by the following claims.

What is claimed is:

1. A medical device, comprising:
   a needle, including a plurality of links and a distal tip, reciprocally movable between a first configuration and a second configuration;
   a spring configured to bias the needle to the first configuration;
   a conduit including a lumen and extending through the needle, the conduit being coupled to the distal tip, wherein longitudinal movement of the conduit is configured to transition the needle between the first configuration and the second configuration, wherein the plurality of links are aligned straight relative to one another when the needle is in the first and second configurations; and
   wherein the needle has a first rigidity in the first configuration, and a second rigidity greater than the first rigidity in the second configuration.

2. The medical device of claim 1, wherein application of a force to the distal tip in the first configuration causes the plurality of links and the distal tip to change orientation relative to one another, and application of the force to the distal tip in the second configuration does not cause the plurality of links and the distal tip to change orientation relative to one another.

3. The medical device of claim 1, wherein fluid flow through the needle passes through the lumen of the conduit, and exits the needle only at the distal tip.

4. The medical device of claim 1, wherein the plurality of links ride loosely along an outer surface of the conduit in the first configuration.

5. The medical device of claim 1, wherein a proximal force applied to the conduit while the needle is in the first configuration compresses the spring and transitions the needle into the second configuration.

6. The medical device of claim 5, wherein release of the proximal force while the needle is in the second configuration allows the needle to transition back to the first configuration.

7. The medical device of claim 5, further including a handle having a body, an actuator movable relative to the body, a first stop on an outer surface of the conduit, a second stop extending radially inward from an inner surface of the body, wherein the spring is between the first stop and the second stop.

8. The medical device of claim 7, wherein the conduit is coupled to a distal end of the actuator.

9. The medical device of claim 1, wherein the longitudinal movement of the conduit is relative to the plurality of links.

10. The medical device of claim 1, wherein the conduit is fixed to the distal tip.

11. The medical device of claim 1, wherein at least one of the plurality of links has a protrusion that engages a surface of an adjacent link.

12. The medical device of claim 1, wherein the needle has a greater length in the first configuration than in the second configuration.

13. The medical device of claim 1, wherein the needle tip includes a distalmost point splayed radially outward from a remainder of the distal tip, wherein the distalmost point is located at an end of a path that travels along an entirety of the needle.

14. A medical device, comprising:
  a needle, including a plurality of links and a distal tip, reciprocally movable between a first configuration and a second configuration, wherein second configuration is more rigid than the first configuration;
  a spring configured to bias the needle to the first configuration; and
  a conduit including a lumen and extending through the needle, the conduit being fixed to the distal tip, wherein application of a proximal pulling force on the conduit is configured to transition the needle from the first configuration and the second configuration, and release of the proximal pulling force is configured to transition the needle from the second configuration to the first configuration, wherein the plurality of links are aligned straight relative to one another when the needle is in the first and second configurations.

15. The medical device of claim 14, wherein application of a force to the distal tip in the first configuration causes the plurality of links and the distal tip to change orientation relative to one another, and application of the force to the distal tip in the second configuration does not cause the plurality of links and the distal tip to change orientation relative to one another.

16. The medical device of claim 14, wherein fluid flow through the needle passes through the lumen of the conduit, and exits the needle only at the distal tip.

* * * * *